United States Patent
Kuwabara et al.

(10) Patent No.: US 12,174,662 B2
(45) Date of Patent: Dec. 24, 2024

(54) WEARABLE SENSOR DEVICE AND MONITORING SYSTEM

(71) Applicant: Nippon Telegraph and Telephone Corporation, Tokyo (JP)

(72) Inventors: Kei Kuwabara, Tokyo (JP); Akio Tokura, Tokyo (JP); Takako Ishihara, Tokyo (JP); Toshiki Wada, Tokyo (JP); Yuichi Higuchi, Tokyo (JP); Yuki Hashimoto, Tokyo (JP); Hiroyoshi Togo, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 53 days.

(21) Appl. No.: 17/773,959

(22) PCT Filed: Nov. 6, 2019

(86) PCT No.: PCT/JP2019/043411
§ 371 (c)(1),
(2) Date: May 3, 2022

(87) PCT Pub. No.: WO2021/090386
PCT Pub. Date: May 14, 2021

(65) Prior Publication Data
US 2022/0382325 A1 Dec. 1, 2022

(51) Int. Cl.
*G06F 1/16* (2006.01)
*G06F 1/18* (2006.01)
*H04W 4/38* (2018.01)

(52) U.S. Cl.
CPC .............. *G06F 1/163* (2013.01); *G06F 1/181* (2013.01); *H04W 4/38* (2018.02)

(58) Field of Classification Search
CPC .......... G06F 1/163; G06F 1/181; H04W 4/38; G01K 1/024; G01K 1/08; G01K 1/14;
(Continued)

(56) References Cited

U.S. PATENT DOCUMENTS 5,396,796 A 3/1995 Kotani et al.
10,485,475 B1 * 11/2019 Miller .................. A61B 5/1455
(Continued)

FOREIGN PATENT DOCUMENTS

DE 19619667 A1 11/1996
EP 1734858 B1 7/2014
(Continued)

OTHER PUBLICATIONS

Nicole, "Tutorial: Covering snaps with thick fabric", Dec. 26, 2016, http://www.nicoleathome.com/2016/12/tutorial-covering-snaps-with-thick.html?m=1 (Year: 2016).*

*Primary Examiner* — Rockshana D Chowdhury
*Assistant Examiner* — Martin Antonio Asmat Uceda
(74) *Attorney, Agent, or Firm* — Slater Matsil, LLP

(57) ABSTRACT

A wearable sensor device includes a temperature and humidity sensor that measures ambient environmental information around a living body. The temperature and humidity sensor is provided on an outer wall surface of a housing or provided to be separated from the outer wall surface. The outer wall surface of the housing faces a left or right side or diagonally downward when the wearable sensor device is attached to the living body and the living body is in a standing posture.

9 Claims, 6 Drawing Sheets

(58) Field of Classification Search
CPC .......... G01K 13/02; A41D 1/002; A61B 5/01; A61B 5/6801; A61B 5/6804; A61B 5/681; A61B 5/4875; A61B 2560/0242; G01F 1/684; G01J 5/041; G01R 1/04
See application file for complete search history.

(56) References Cited

U.S. PATENT DOCUMENTS

| | | | |
|---|---|---|---|
| 11,493,889 B2* | 11/2022 | Yang | ........................ H05K 1/115 |
| 2005/0245839 A1* | 11/2005 | Stivoric | ............. A61B 10/0012 |
| | | | 374/E1.004 |
| 2014/0139637 A1* | 5/2014 | Mistry | ................... H04N 23/51 |
| | | | 348/46 |
| 2016/0140870 A1 | 5/2016 | Connor | |
| 2017/0352242 A1* | 12/2017 | Glynn | ................. G08B 21/0469 |
| 2018/0220950 A1* | 8/2018 | Cobanoglu | ............ G08C 17/02 |

FOREIGN PATENT DOCUMENTS

| | | | |
|---|---|---|---|
| JP | H04113093 U | | 10/1992 |
| JP | H07015719 U | | 3/1995 |
| JP | 2006055189 A | * | 3/2006 |
| JP | 2007073020 A | | 3/2007 |
| JP | 2017070666 A | | 4/2017 |
| JP | 2017529133 A | | 10/2017 |
| JP | 2018109553 A | | 7/2018 |
| JP | 2018109594 A | | 7/2018 |
| WO | 2016025851 A1 | | 2/2016 |
| WO | 2019014166 A1 | | 1/2019 |

* cited by examiner

WEARABLE SENSOR DEVICE AND MONITORING SYSTEM

CROSS-REFERENCE TO RELATED APPLICATIONS

This application is a national phase entry of PCT Application No. PCT/JP2019/043411, filed on Nov. 6, 2019, which application is hereby incorporated herein by reference.

TECHNICAL FIELD

The present invention relates to a wearable sensor device and a monitoring system that measure ambient environmental information around a living body.

BACKGROUND

It is important to monitor environmental information for physical condition management such as prevention of heat stroke in hot weather.

For example, a heat index meter conventionally used for preventing heat stroke measures a black bulb temperature, a wet bulb temperature, and a dry bulb temperature to obtain a heat index (see Non-Patent Literature 1). Non-Patent Literature 1 discloses a method using the heat index as a guideline for action, such as avoiding going out or strenuous work when the heat index is relatively high.

Conventional heat index meters are generally configured as relatively large devices and it is difficult to place them in any given location. For example, the heat index released by the Ministry of the Environment is a value that represents a wide area.

However, the heat load actually experienced by an individual is greatly affected by the local environment. For example, the environment varies greatly depending on where each person is, such as outdoors or indoors, in sunshine or shade, and on lawn or concrete. Moreover, even in the same place, the influence of radiation from, for example, the ground differs greatly from a tall adult to a short child. Furthermore, the environment around a human body changes greatly depending on the clothes that the person is wearing, the kinetic condition, and the sweating condition.

Therefore, a method is conceivable in which a person who wants to manage his or her physical condition carries or wears an environmental sensor to monitor the environment around the human body. However, conventional environmental sensors have problems such as inconvenience in carrying, the inability to perform accurate measurement when sweat adheres to the sensor, and the inability to accurately measure original ambient environmental information around a human body if air permeability is obstructed due to attachment of an environmental sensor.

CITATION LIST

Non-Patent Literature

Non-Patent Literature 1: JuYoun Kwon, Ken Parsons, "Evaluation of the Wet Bulb Globe Temperature (WBGT) Index for Digital Fashion Application in Outdoor Environments", Journal of the Ergonomics Society of Korea, 36(1), pp. 23-36, 2017.

SUMMARY

Technical Problem

Embodiments of the present invention have been made to solve the above-mentioned problems, and an object of the present invention is to enable ambient environmental information around a living body to be measured easily, stably, and accurately.

Means for Solving the Problem

A wearable sensor device of embodiments of the present invention includes an environmental sensor configured to measure ambient environmental information around a living body, wherein the environmental sensor is provided on an outer wall surface of a housing or provided to be separated from the outer wall surface, the outer wall surface facing a left or right side or diagonally downward when the wearable sensor device is attached to the living body and the living body is in a standing posture.

Effects of Embodiments of the Invention

According to embodiments of the present invention, the environmental sensor is provided on the outer wall surface of the housing facing a left or right side or diagonally downward of the living body when the living body is in the standing posture, or is provided to be separated from the outer wall surface. This makes it possible to measure local ambient environmental information around the living body easily and stably.

DETAILED DESCRIPTION OF ILLUSTRATIVE EMBODIMENTS

Hereinafter, preferred embodiments of the present invention will be described in detail with reference to the drawings.

First Embodiment

Figure 1A:
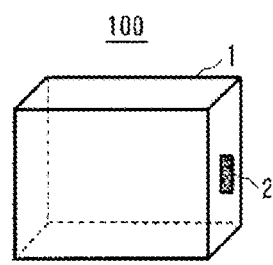
FIG. 1A is a front perspective view of a wearable sensor device according to a first embodiment of the present invention.
Figure 1B:
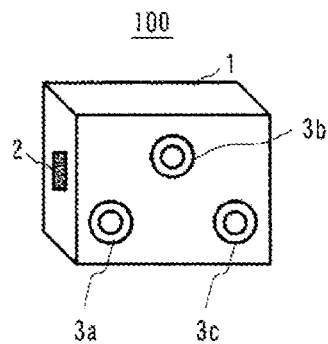
FIG. 1B is a rear perspective view of the wearable sensor device according to the first embodiment of the present invention.

FIG. 1A is a front perspective view of a wearable sensor device according to a first embodiment of the present invention, and FIG. 1B is a rear perspective view of the wearable sensor device. Here, the surface of a wearable sensor device 100 facing an innerwear worn on the wearer is referred to as a back surface, and the surface opposite to the back surface is referred to as a front surface of the wearable sensor device 100.

The wearable sensor device 100 includes a temperature and humidity sensor 2 (environmental sensor) on the side surface of an outer wall of a sealed housing 1. Further, as will be described later, three snap buttons 3a, 3b, and 3c (first coupling members) for attaching the wearable sensor device 100 to the innerwear are provided on the back surface of the outer wall of the housing 1 facing the innerwear.

Figure 2:
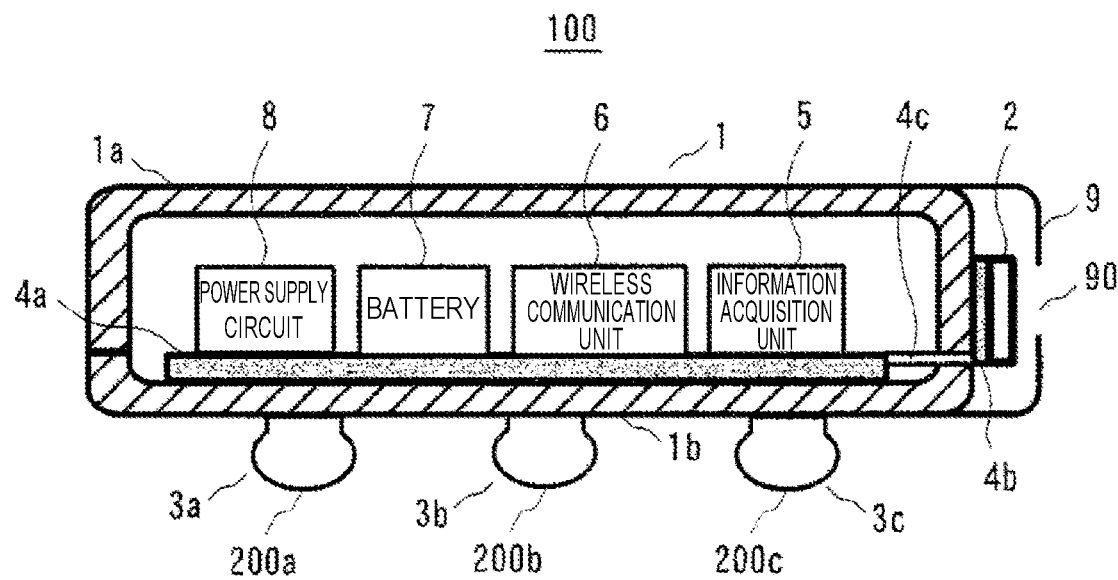
FIG. 2 is a diagram illustrating an inner structure of the wearable sensor device according to the first embodiment of the present invention.

FIG. 2 is a diagram illustrating an inner structure of the wearable sensor device 100. The wearable sensor device 100 includes a rigid substrate 4a and a flexible substrate 4c for connecting a circuit mounted on the rigid substrate 4a and the temperature and humidity sensor 2 in the sealed housing 1.

An information acquisition unit 5 for processing environmental information measured by the temperature and humidity sensor 2, a wireless communication unit 6 for wirelessly transmitting the environmental information to an external device, a battery 7, and a power supply circuit 8 for supplying a power supply voltage to the circuit on the rigid substrate 4a and the temperature and humidity sensor 2 using the voltage of the battery 7 as an input are mounted on the rigid substrate 4a.

The housing 1 is sealed and has waterproofness so that liquids such as sweat and rain do not enter from the outside. The housing 1 includes a resin-made upper lid 1a, for example, and similarly a resin-made lower lid 1b. As a well-known method for ensuring the waterproofness of the housing 1, a method of screwing the upper lid 1a to the lower lid 1b with an O-ring inserted between the upper lid 1a and the lower lid 1b, a method of fixing the upper lid 1a and the lower lid 1b together with an adhesive, a method of ultrasonic-bonding the upper lid 1a and the lower lid 1b, and the like may be used.

The temperature and humidity sensor 2 is mounted on a rigid substrate 4b. The rigid substrate 4b is fixed to the side surface of the outer wall of the housing 1. The temperature and humidity sensor 2 includes, for example, a semiconductor chip. The semiconductor chip is equipped with a temperature sensor of which the resistance changes with temperature and a humidity sensor that absorbs moisture in the surrounding gas so that the capacitance or resistance changes. The temperature and humidity sensor 2 mounted on the rigid substrate 4b is electrically connected to the information acquisition unit 5 and the power supply circuit 8 inside the housing 1 via a flexible wiring and a wiring on the rigid substrate 4a. As the flexible wiring, for example, the flexible substrate 4c can be used.

The rigid substrates 4a and 4b and the flexible substrate 4c are integrated to form a rigid flexible substrate. As described above, the information acquisition unit 5, the wireless communication unit 6, the battery 7, and the power supply circuit 8 are mounted on the rigid substrate 4a, the temperature and humidity sensor 2 is mounted on the rigid substrate 4b, and the rigid substrate 4a and the rigid substrate 4b are electrically connected by the flexible substrate 4c.

The rigid substrate 4a is fixed to an inner wall surface of the lower lid 1b. The rigid substrate 4b is fixed to the side surface of an outer wall of the lower lid 1b. With the rigid substrates 4a and 4b fixed to the lower lid 1b, the flexible substrate 4c is sandwiched between the upper lid 1a and the lower lid 1b, and the upper lid 1a and the lower lid 1b are attached by methods such as screwing, adhesion, or ultrasonic bonding.

Further, as illustrated in FIG. 2, for example, a resin-made protective member 9 may be provided around the temperature and humidity sensor 2. The protective member 9 plays a role of preventing the temperature and humidity sensor 2 from colliding with an external object and being damaged, or preventing a person's finger or the like from coming into contact with the surface of the temperature and humidity sensor 2 and contaminating the sensor surface. The protective member 9 is fixed to the side surface of the outer wall of the housing 1. The protective member 9 is provided with a ventilation hole 90. Since the temperature and humidity sensor 2 can come into contact with the outside air through the ventilation hole 90, it is possible to measure the temperature and humidity of the surrounding air.

In this way, temperature and humidity data (environmental information) measured by the temperature and humidity sensor 2 can be transmitted to the information acquisition unit 5 inside the housing 1 and be processed.

In the present embodiment, the temperature and humidity sensor 2 having a built-in AD converter is used, and the measured value of the temperature and humidity is converted into digital data by the AD converter and transmitted to the information acquisition unit 5. The configuration of the temperature and humidity sensor 2 is not limited to this embodiment, and an analog-output temperature and humidity sensor may be used. In this case, an analog signal processing unit or an AD converter may be mounted on the rigid substrate 4a, and the analog signals output from the temperature and humidity sensor 2 may be processed (for example, amplified) by the analog signal processing unit and then converted to digital data by the AD converter and passed to the information acquisition unit 5.

The metal-made snap buttons 3a, 3b, and 3c are machined in advance as individual parts. Then, the snap buttons 3a, 3b, and 3c are integrated with the lower lid 1b by an insert molding method so that, when the resin-made lower lid 1b is manufactured, convex portions 200a, 200b, and 200c protrude from the lower surface of the outer wall of the lower lid 1b, and the remaining portion is surrounded by the lower lid 1b. In this way, the snap buttons 3a, 3b, and 3c can be fixed to the lower lid 1b while ensuring the waterproofness of the portion to which the snap buttons 3a, 3b, and 3c are fixed.

Figure 3:
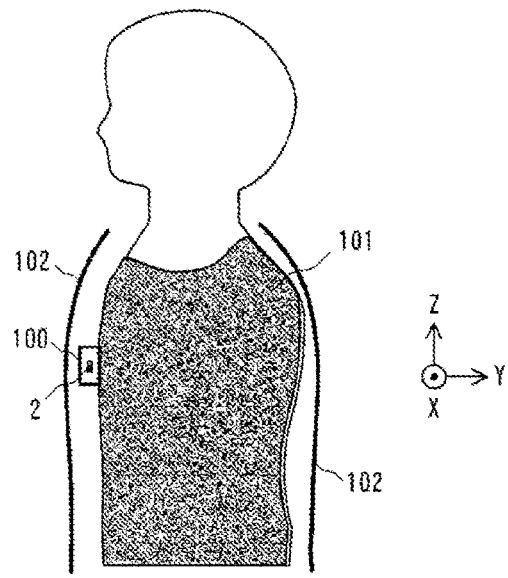
FIG. 3 is a diagram illustrating a state in which a wearer is wearing the wearable sensor device in the first embodiment of the present invention.
Figure 4:
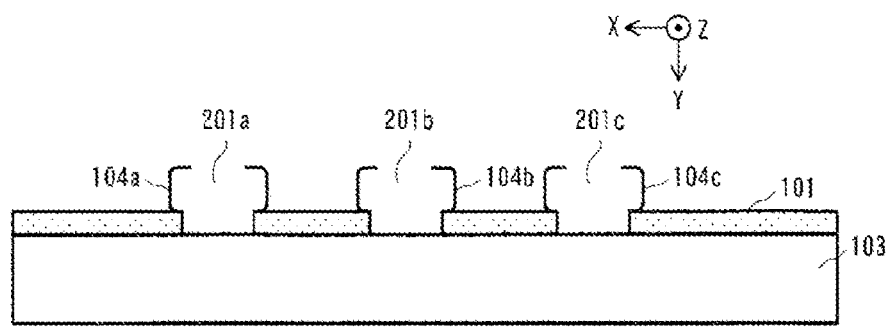
FIG. 4 is an enlarged view of the wear in a state in which the wearer is not wearing the wearable sensor device.
Figure 5:
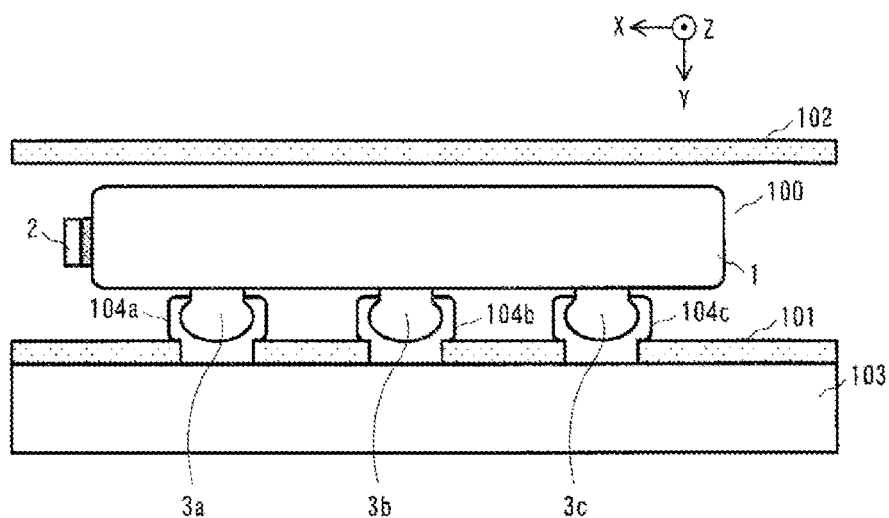
FIG. 5 is an enlarged view of the wearable sensor device and the wear in a state in which the wearer is wearing the wearable sensor device.
Figure 6:
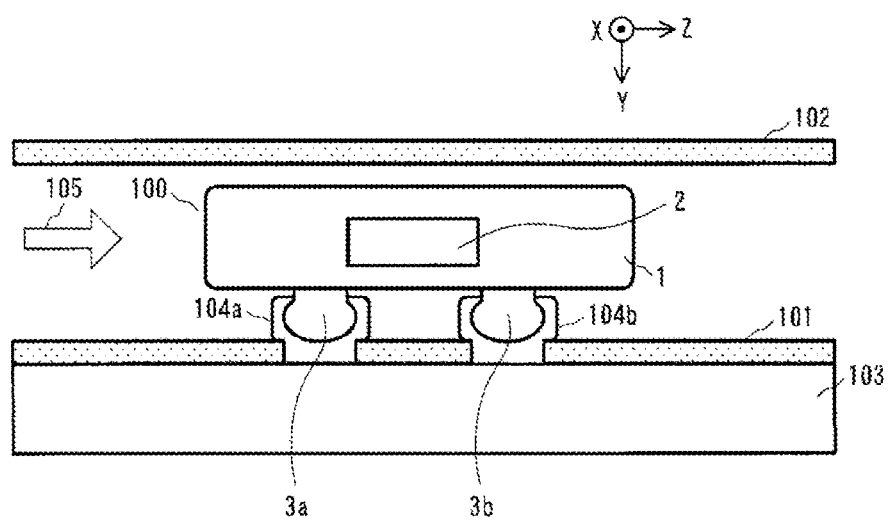
FIG. 6 is an enlarged view of the wearable sensor device and the wear in a state in which the wearer is wearing the wearable sensor device.

FIG. 3 is a diagram illustrating a state in which the wearer is wearing the wearable sensor device 100. FIG. 4 is an enlarged view of the wear in a state in which the wearer is not wearing the wearable sensor device 100. FIGS. 5 and 6 are enlarged views of the wearable sensor device 100 and the wear in a state in which the wearer is wearing the wearable sensor device 100. In FIGS. 3 to 6, the left-right direction of the wearer's body is the X direction, the front-back direction is the Y direction, and the vertical direction is the Z direction.

FIGS. 3, 5, and 6 illustrate a state in which the wearer attaches the wearable sensor device 100 to an innerwear 101 such as a T-shirt, and wears an outerwear 102 on the innerwear 101. FIG. 5 illustrates a state in which a portion between the outerwear 102 and the innerwear 101 is viewed from the wearer's head. FIG. 6 illustrates a state in which a portion between the outerwear 102 and the innerwear 101 is viewed from the left side of the wearer's body. In addition, in FIGS. 3, 5, and 6, the protective member 9 is not illustrated.

The innerwear 101 is provided with snap buttons 104a, 104b, and 104c (second coupling member) provided so that concave portions 201a, 201b, and 201c are exposed to the surface opposite to the surface in contact with a wearer's skin 103.

As illustrated in FIGS. 5 and 6, the convex portions of the male snap buttons 3a, 3b, and 3c provided on the wearable sensor device 100 and the concave portions of the female snap buttons 104a, 104b, and 104c provided on the innerwear 101 are fitted. As a result, the wearable sensor device 100 can be easily attached to the innerwear 101. When the wearable sensor device 100 is attached to the innerwear 101, the wearable sensor device 100 and the innerwear 101 form a monitoring system that measures ambient environmental information around the wearer.

Since the wearable sensor device 100 has a thickness of, for example, about 5 mm to 10 mm, it is possible to measure ambient environmental information such as temperature and humidity around a human body without interfering with the movement of the wearer. Further, since the snap buttons 3a, 3b, and 3c are detachably connectable to the snap buttons 104a, 104b, and 104c, when the innerwear 101 is attempted to be washed, the wearable sensor device 100 can be removed and only the innerwear 101 is washed.

When the wearer is wearing the outerwear 102 on the innerwear 101 as illustrated in FIGS. 3, 5, and 6, the wearable sensor device 100 is provided between the innerwear 101 and the outerwear 102.

A gap is formed between the innerwear 101 and the outerwear 102 due to the deflection of the wears 101 and 102 and the thickness of the wearable sensor device 100. As described above, the temperature and humidity sensor 2 is provided on the side surface of the outer wall of the wearable sensor device 100. Since the back surface of the outer wall provided with the snap buttons 3a, 3b, and 3c of the wearable sensor device 100 and the side surface of the outer wall provided with the temperature and humidity sensor 2 are substantially orthogonal to each other, the temperature and humidity sensor 2 is arranged on a surface near the wearer's body surface, which is substantially orthogonal to the body surface, when the wearable sensor device 100 is attached to the innerwear 101.

Therefore, the temperature and humidity sensor 2 faces the space formed between the innerwear 101 and the outerwear 102, and can measure the environmental information of this space.

If the temperature and humidity sensor 2 is arranged on the same surface as or the surface opposite to the snap buttons 3a, 3b, and 3c of the wearable sensor device 100, the air permeability around the temperature and humidity sensor 2 is reduced when the wearable sensor device 100 is attached to the innerwear 101. As a result, the temperature and humidity sensor 2 measures information different from the original ambient environmental information around the wearer. When the temperature and humidity sensor 2 is arranged on a surface substantially orthogonal to the wearer's body surface as in the present embodiment, the problem of reduced air permeability can be solved.

As illustrated in FIGS. 3, 5, and 6, the temperature and humidity sensor 2 is arranged on the surface of the housing 1 that faces the wearer's body in the left-right direction when the wearer is in a standing posture.

If the temperature and humidity sensor 2 is arranged on the surface of the housing 1 facing upward when the wearer is in a standing posture, sweat adheres to the temperature and humidity sensor 2 and its surroundings, and cases where the humidity is measured high are likely to occur. Therefore, by arranging the temperature and humidity sensor 2 on the surface of the housing 1 other than the surface facing upward when the wearer is in the standing posture, it is possible to avoid the problem that the measurement is inaccurate due to the adhesion of sweat or the like.

Further, the air between the innerwear 101 and the outerwear 102 is ventilated with the outside air by a lower opening and an upper opening of the outerwear 102. Airflow mainly in the vertical direction is generated between the innerwear 101 and the outerwear 102 to ventilate the air. Arrow 105 in FIG. 6 indicates the airflow between the innerwear 101 and the outerwear 102.

On the surface of the housing 1 facing downward when the wearer is in a standing position, the airflow between the innerwear 101 and the outerwear 102 is blocked by the wearable sensor device 100, and the air is stagnant. Therefore, if the temperature and humidity sensor 2 is arranged on the surface of the housing 1 facing downward when the wearer is in the standing posture, information different from the original ambient environmental information around the wearer is measured.

By arranging the temperature and humidity sensor 2 on the surface of the housing 1 facing the left side of the wearer's body when the wearer is in the standing posture as in the present embodiment, air flows around the temperature and humidity sensor 2 without the airflow being blocked between the innerwear 101 and the outerwear 102. As a result, the temperature and humidity sensor 2 can measure the original ambient environmental information around the wearer.

In FIGS. 3, 5, and 6, the temperature and humidity sensor 2 is arranged on the surface of the housing 1 facing the left side of the wearer's body when the wearer is in the standing posture. However, the temperature and humidity sensor 2 may naturally be arranged on the surface of the housing 1 facing the right side of the wearer's body.

Next, a circuit configuration of the wearable sensor device 100 will be described with reference to FIG. 7. In the present embodiment, the temperature and humidity sensor 2 is connected to the information acquisition unit 5. The information acquisition unit 5 includes a memory 50 for storing information.

The information acquisition unit 5 delivers the temperature and humidity data measured by the temperature and humidity sensor 2 to the wireless communication unit 6. At this time, naturally, the information acquisition unit 5 may temporarily store the temperature and humidity data in the memory 50 and deliver the temperature and humidity data to the wireless communication unit 6 when the timing to transmit the temperature and humidity data comes.

The wireless communication unit 6 wirelessly transmits the temperature and humidity data measured by the temperature and humidity sensor 2 from an antenna 60 to an external device. An example of a destination external device is a smartphone possessed by the wearer.

Figure 7:
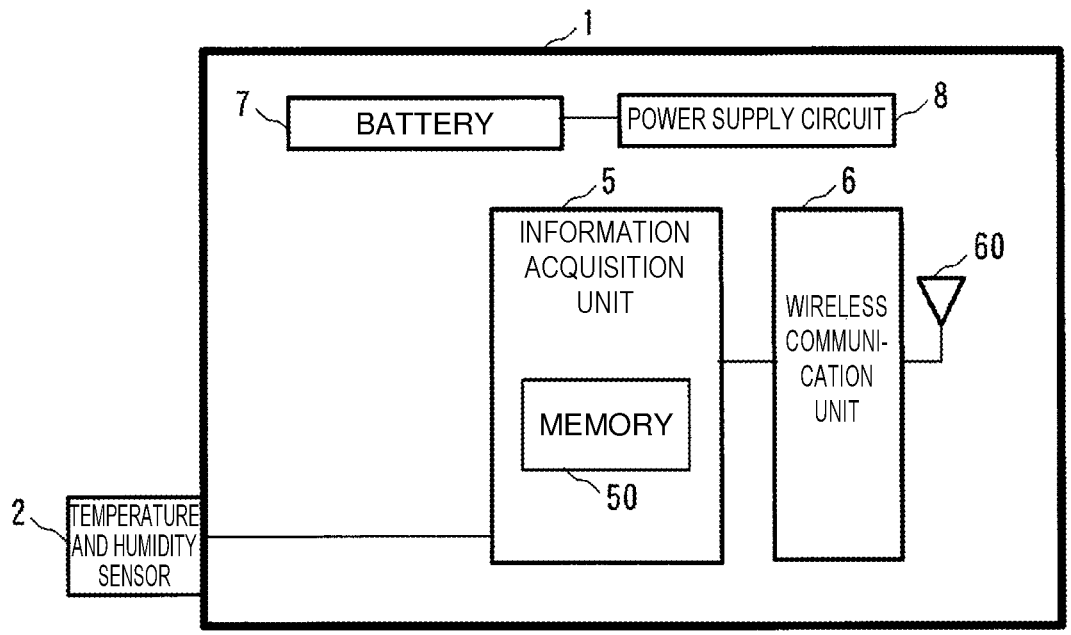
FIG. 7 is a block diagram illustrating a circuit configuration of the wearable sensor device according to the first embodiment of the present invention.

Although the information acquisition unit 5 and the wireless communication unit 6 are described as separate blocks in FIG. 7, one semiconductor chip having the functions of the information acquisition unit 5 and the wireless communication unit 6 may be used.

The snap buttons 3a, 3b, and 3c are arranged in a non-point-symmetry with respect to the surface of the housing 1 on which they are provided (there is no symmetry point on the surface of the housing 1). In particular, in the present embodiment, the snap buttons 3a, 3b, and 3c are arranged one by one at each vertex position of the isosceles triangle (excluding the equilateral triangle) in a plan view. Therefore, the snap buttons 104a, 104b, and 104c that fit with the snap buttons 3a, 3b, and 3c are also arranged one by one at each vertex position of the isosceles triangle (excluding the equilateral triangles) in the plan view on the surface of the innerwear 101. With such an arrangement, the snap buttons 3a, 3b, and 3c and the snap buttons 104a, 104b, and 104c can be correctly fitted, and the temperature and humidity sensor 2 can be prevented from being mounted in the wrong direction.

Second Embodiment

Figure 8A:
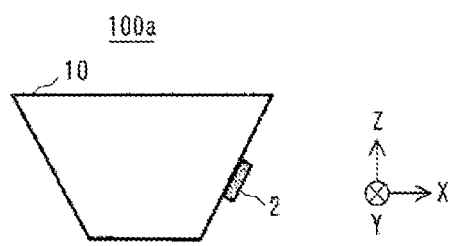
FIG. 8A is a front view of a wearable sensor device according to a second embodiment of the present invention.
Figure 8B:
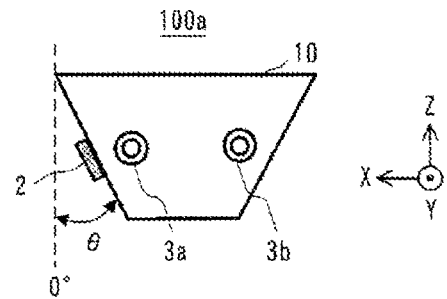
FIG. 8B is a rear view of the wearable sensor device according to the second embodiment of the present invention.

Next, a second embodiment of the present invention will be described. FIG. 8A is a front view of a wearable sensor device according to the second embodiment of the present invention. FIG. 8B is a rear view of the wearable sensor device. In FIGS. 8A and 8B, the left-right direction of the wearer's body is the X direction, the front-back direction is the Y direction, and the vertical direction is the Z direction, as in the first embodiment.

A circuit configuration of a wearable sensor device 100a is the same as that of the first embodiment. In the present embodiment, the temperature and humidity sensor 2 is arranged on the surface of a housing 10 facing in a diagonally downward direction of the wearer's body when the wearable sensor device 100a is attached to the wear worn on the wearer and the wearer is in a standing posture. Due to such an arrangement, in the present embodiment, the possibility of sweat adhering to the temperature and humidity sensor 2 or the periphery thereof can be reduced as compared with the case where the temperature and humidity sensor 2 is arranged on the surface of the housing 10 facing the left or right side of the wearer's body as in the first embodiment. Further, in the present embodiment, it is possible to avoid the airflow around the temperature and humidity sensor 2 from being blocked and becoming stagnant as in the case where the temperature and humidity sensor 2 is arranged on the surface of the housing 10 facing downward when the wearer is in the standing posture.

In order to prevent sweat from adhering to the temperature and humidity sensor 2 and prevent stagnation of airflow, it is preferable that the surface of the housing 10 on which the temperature and humidity sensor 2 is arranged has an angle θ in the range of, for example, θ=20° to 90° from the vertically downward direction (0°) when the wearable sensor device 100a is attached to the wearer's wear and the wearer is in a standing position. More preferably, by setting the range of θ=30° to 60°, it is possible to more reliably prevent the adhesion of sweat to the temperature and humidity sensor 2 and the stagnation of the airflow.

In the present embodiment, two snap buttons 3a and 3b are arranged on the back surface of the wearable sensor device 100a. When there are two snap buttons 3a and 3b, the wearable sensor device 100a may be attached to the wear in an upside-down state. In cope with such a problem, in the present embodiment, the housing 10 has an asymmetrical shape. Specifically, the housing 10 narrows from top to bottom. By making the housing 10 asymmetrical in this way, it becomes easy to prevent the wearable sensor device 100a from being attached in a wrong direction, and urge the temperature and humidity sensor 2 to be attached so as to face diagonally downward of the wearer's body.

Further, in order to prevent the wearable sensor device 100a from being attached to the wear in an upside-down state, a mark indicating the vertical direction of the wearable sensor device 100a may be provided on the surface of the housing.

Further, a mark or the like indicating the direction of wearing may be provided on the wear to which the wearable sensor device 100a is attached.

In the first and second embodiments, an example in which a snap button is used as a coupling member of the wearable sensor device boo or 100a to the wear is illustrated, but the present invention is not limited thereto, and a coupling member such as, for example, a magnet, a clip, or the Magic Tape (registered trademark) may be used. The wearable sensor device 100 or 100a can be attached to the wear using these coupling members. Alternatively, a pocket may be provided on the wear side for attachment of the wearable sensor device instead of a coupling member provided on the wearable sensor device itself.

Further, a patch or the like that can be adhered to the skin may be provided on the back surface of the wearable sensor device 100 or 100a so that the wearable sensor device 100 or 100a can be directly attached to the wearer's body surface instead of a wear. Further, the wearable sensor device 100 or 100a may be integrated with the wear without being detachably attached thereto.

Further, the wearable sensor device 100 or 100a can be attached to various wears such as a T-shirt, a tank top, a belly band, a belt around the chest, trousers, an underwear, and an outerwear. The wearable sensor device 100 or 100a may also be attached to socks, a hat, a helmet and the like.

Further, since the wearable sensor devices 100 and 100a are intended to monitor the ambient environmental information around a living body, the devices may be worn on an animal or the like without being limited to a person.

Further, in the first and second embodiments, an example of a temperature and humidity sensor is illustrated as an environmental sensor. However, the present invention is not limited thereto, and an environmental sensor such as a temperature sensor alone, a humidity sensor alone, a barometric pressure sensor, or a gas sensor may be used. Further, a composite sensor in which a number of these sensors are combined may be used as an environmental sensor.

Further, in the first and second embodiments, an example in which environmental information is transmitted to an external device by the wireless communication unit 6 is illustrated, but the present invention is not limited thereto.

The information acquisition unit 5 may store the measured environmental information in the memory 50. In this case, the wearable sensor device can be removed from the wear after the measurement, and the environmental information stored in the memory 50 can be read by wire. Naturally, in the case of reading the information by wire, it is necessary to provide a reading connector electrically connected to the information acquisition unit 5 in the housing.

Further, in the first and second embodiments, a structure in which the rigid substrate 4a and the flexible substrate 4b are covered and sealed with the box-shaped housing 1 is illustrated as an example, but the present invention is not limited thereto. For example, a resin or the like may be poured around the rigid substrate 4a, the flexible substrate 4b, and the snap buttons 3a, 3b, and 3c to cure the resin and achieve sealing.

Figure 9:
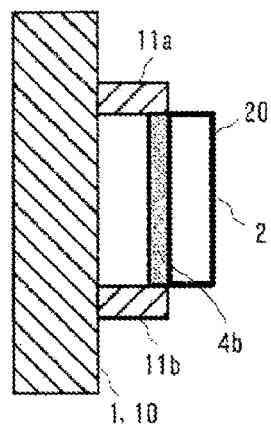
FIG. 9 is a diagram illustrating another method of fixing a temperature and humidity sensor according to the first and second embodiments of the present invention.

Further, in the first and second embodiments, the temperature and humidity sensor 2 is mounted on the rigid substrate 4b, and the rigid substrate 4b is fixed to the outer wall surface of the housing 1 or 10, but the present invention is not limited thereto. As illustrated in FIG. 9, the temperature and humidity sensor 2 may be provided to be separated from the outer wall surface so that the sensor surface 20 of the temperature and humidity sensor 2 is parallel to the outer wall surface of the housing 1 or 10.

Specifically, support members 11a and 11b that support the rigid substrate 4b may be provided on the outer wall surface of the housing 1 or 10 so that the rigid substrate 4b on which the temperature and humidity sensor 2 is mounted is provided on the outer wall surface of the housing 1 or 10 with a space therebetween. In this way, the temperature and humidity sensor 2 can be provided to be separated from the outer wall surface by the support members 11a and 11b.

Figure 10:
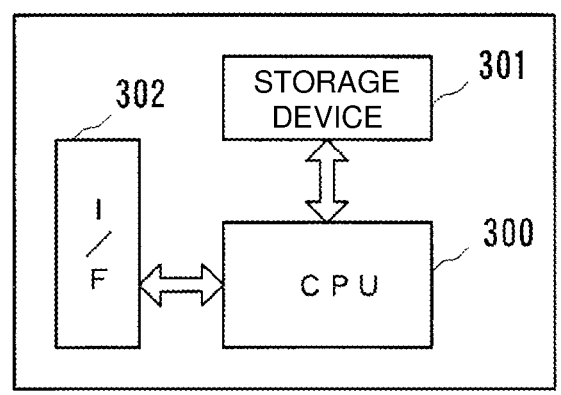
FIG. 10 is a block diagram illustrating a configuration example of a computer that realizes the wearable sensor device according to the first and second embodiments of the present invention.

In the configurations of the wearable sensor devices 100 and 100a described in the first and second embodiments, the software functions of the information acquisition unit 5 and the wireless communication unit 6 can be realized by a computer provided with a CPU (Central Processing Unit), a storage device, and an interface, and a program that controls these hardware resources. A configuration example of this computer is illustrated in FIG. 10.

The computer includes a CPU 300, a storage device 301, and an interface device (I/F) 302. The interface device 302 is connected to hardware components including the temperature and humidity sensor 2 and the wireless communication unit 6. In such a computer, a program for realizing a monitoring method of embodiments of the present invention is stored in the storage device 301. The CPU 300 executes the process described in the first and second embodiments according to the program stored in the storage device 301.

INDUSTRIAL APPLICABILITY

Embodiments of the present invention can be applied to a technique for measuring environmental information.

REFERENCE SIGNS LIST 1, 10 Housing
1a Upper lid
1b Lower lid
2 Temperature and humidity sensor
3a to 3c, 104a to 104c Snap button
4a, 4b Rigid substrate
4c Flexible substrate
5 Information acquisition unit
6 Wireless communication unit
7 Battery
8 Power supply circuit
9 Protective member
11a, 11b Support member
50 Memory
90 Ventilation hole
100, 100a Wearable sensor device
101 Innerwear
102 Outerwear.

The invention claimed is:

1. A wearable sensor device comprising
a housing including an outer wall surface, the outer wall surface including a back surface which faces a living body, a front surface opposite to the back surface, and side surfaces, the side surfaces including a first side surface and a second side surface being shaped such that distance between the first side surface and the second side surface decreases from top to bottom when viewed from a side of the back surface;
an environmental sensor configured to measure ambient environmental information around the living body; and
a first coupling member configured to attach the wearable sensor device to the living body,
wherein the environmental sensor is provided on the first side surface of the outer wall surface of the housing, or provided to be separated from and facing the first side surface of the outer wall surface,
wherein an angle formed by the first side surface and a vertical direction is in a range of 30° to 60° when a lower end of the first side surface and a lower end of the second side surface are arranged horizontally from each other, and
wherein the first coupling member is provided only on the back surface of the outer wall surface of the housing.

2. The wearable sensor device according to claim 1, further comprising a wireless communication device configured to wirelessly transmit the ambient environmental information to an external device, wherein:
the housing is sealed; and
the wireless communication device is provided in the housing.

3. The wearable sensor device according to claim 1, further comprising a protective member having a ventilation hole around the environmental sensor.

4. The wearable sensor device according to claim 1, wherein:
the environmental sensor and the first coupling member are provided on respective surfaces of the housing that are orthogonal to each other; and
the environmental sensor is provided on an outer wall surface of the housing or provided to be separated from the outer wall surface, the outer wall surface being orthogonal to a body surface of the living body when the wearable sensor device is attached to the living body.

5. A monitoring system comprising:
a wearable sensor device comprising:
a housing including an outer wall surface, the outer wall surface including a back surface which faces a living body, a front surface opposite to the back surface, and side surfaces the side surfaces including a first side surface and a second side surface being shaped such that distance between the first side surface and the second side surface decreases from top to bottom when viewed from a side of the back surface;
an environmental sensor configured to measure ambient environmental information around the living body; and
a first coupling member configured to attach the wearable sensor device to the living body, wherein the environmental sensor is provided on the first side surface of the outer wall surface of the housing, or provided to be separated from and facing the first side surface of the outer wall surface, wherein an angle formed by the first side surface and a vertical direction is in a range of 30° to 60° when a lower end of the first side surface and a lower end of the second side surface are arranged horizontally from each other, and wherein the first coupling member is provided only on the back surface of the outer wall surface of the housing; and a wear to be worn on the living body, wherein the wear includes a second coupling member provided so as to be fitted with the first coupling member of the wearable sensor device.

6. The monitoring system according to claim 5, wherein: the wear is an innerwear in which the second coupling member is provided on a surface opposite to a surface of the innerwear facing the living body.

7. The monitoring system according to claim 5, wherein the wearable sensor device further comprises a wireless communication device configured to wirelessly transmit the ambient environmental information to an external device, wherein:

the housing is sealed; and the wireless communication device is provided in the housing.

8. The monitoring system according to claim 5, wherein the wearable sensor device further comprises a protective member having a ventilation hole around the environmental sensor.

9. The monitoring system according to claim 5, wherein the environmental sensor and the first coupling member are provided on respective surfaces of the housing that are orthogonal to each other; and the environmental sensor is provided on an outer wall surface of the housing or provided to be separated from the outer wall surface, the outer wall surface being orthogonal to a body surface of the living body when the wearable sensor device is attached to the living body.

* * * * *